US00PP31374P2

(12) United States Plant Patent
Egger

(10) Patent No.: US PP31,374 P2
(45) Date of Patent: Jan. 14, 2020

(54) ***PHYGELIUS* PLANT NAMED 'TNPHYCY'**

(50) Latin Name: ***Phygelius* x *rectus***
Varietal Denomination: TNPHYCY

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,830

(22) Filed: Jan. 18, 2019

(51) Int. Cl.
*A01H 5/02* (2018.01)
*A01H 6/00* (2018.01)

(52) U.S. Cl.
USPC ..... Plt./468
CPC ..... *A01H 6/00* (2018.05)

(58) Field of Classification Search
USPC ..... Plt./468
CPC ..... A01H 5/02
See application file for complete search history.

(56) References Cited

PUBLICATIONS https://issuu.com/monrovia4/docs/monrovia_tool_ kit_aug_20_ final; Aug. 30, 2018; 4 pages.*

* cited by examiner

*Primary Examiner* — Kent L Bell
(74) *Attorney, Agent, or Firm* — Klarquist Sparkman, LLP

(57) ABSTRACT

A new and distinct cultivar of *Phygelius* plant characterized by medium size canary yellow flowers, a long bloom time, an upright, well branched habit, with multiple crowns from the base, clean-looking, deep green foliage, and excellent vigor.

1 Drawing Sheet

Botanical denomination: *Phygelius* x *rectus*.
Variety designation: 'TNPHYCY'.
Trade designation: COLORBURST™ Yellow.

BACKGROUND OF THE INVENTION

The present invention relates to a new and distinct cultivar of *Phygelius*, given the name, 'TNPHYCY'. *Phygelius* is in the family *Scrophulariaceae*. *Phygelius* x *rectus* 'TNPHYCY' is from a controlled cross using *Phygelius* '69-1', a proprietary, unnamed plant as the seed parent, and *Phygelius* '61-1', a proprietary, unnamed plant as the pollen parent. It was part of a controlled breeding program to produce upright, compact habits with high flower count. This cultivar was selected for the medium size canary yellow flowers, high flower count upright and well branched habit, multiple crowns from the base, extended bloom time, and clean-looking, deep green foliage.

Compared to the seed parent, *Phygelius* '69-1', the new cultivar has brighter yellow flowers, earlier blooming, and a higher flower count.

Compared to the pollen parent, *Phygelius* '61-1', the new cultivar has brighter yellow flowers and a higher flower count.

Compared to *Phygelius* x *aequalis* CROFTWAY® Yellow Sovereign 'Croyelsov', (U.S. Plant Pat. No. 18,376), the new cultivar has brighter canary yellow flowers rather than pale yellow flowers and a higher flower count.

Compared to *Phygelius* x *aequalis* 'Yellow Trumpet', an unpatented cultivar, the new cultivar has brighter canary yellow flowers rather than pale yellow flowers.

*Phygelius* 'TNPHYCY' is uniquely distinguished by its:
1. medium size canary yellow flowers,
2. long bloom time,
3. high flower count,
4. upright, well branched habit, with multiple crowns from the base,
5. clean-looking, deep green foliage, and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of a three-year-old *Phygelius* 'TNPHYCY' growing in full sun in the summer in Canby, Oreg.

FIG. 2 shows the same three-year-old *Phygelius* 'TNPHYCY' growing in full sun in the summer in Canby, Oreg.

DETAILED PLANT DESCRIPTION

The following is a detailed description of the new *Phygelius* cultivar based on observations of a 3-year-old specimen grown outside in a trial garden in Canby, Oreg. in July. The color descriptions are all based on The Royal Horticultural Society Colour Chart, 5th edition, 2007, except where general color terms of ordinary dictionary significance are used.

Plant:

*Type.*—Semi-evergreen subshrub.

*Form.*—Upright, branching.

*Cold Hardiness.*—USDA Zone 7-10.

*Size.*—Grows to 87 cm tall and 43 cm wide.

*Vigor.*—Excellent.

*Stem number.*—16 main stems from the crown.

*Stem.*—Upright, grows to 57 cm long and 6.5 cm wide (at the base), glabrous, internodes grow to 7 cm long, Yellow Green 144A blending to Yellow Green 144B tinted with Greyed Orange 165B at base.

*Rooting.*—Plants root easily from stem cuttings.

Leaf:

*Type.*—Simple.

*Arrangement.*—Opposite.

*Shape.*—Ovate to ovate lanceolate.

*Venation.*—Pinnate.

*Margins.*—Serrate.

*Apex.*—Acute.

*Base.*—Cuneate.

*Blade size.*—Grows to 7.1 cm long and 4 cm wide.

*Petiole.*—Grows to 3.1 cm long and 0.3 cm wide, between Yellow Green 144A and Yellow Green 144B.

*Surface texture.*—Glabrous on both sides.

*Leaf color.*—Topside closest to Green N137A with main vein at base Green 137C, bottom side Green 138B.

Inflorescence:

*Type.*—One-sided, pyramidal panicle with pendulous flowers.

*Number of flowers per inflorescence.*—About 80.

*Size of inflorescence.*—Grows to 24 cm long and 7.5 cm wide.

*Peduncle.*—Grows to 2.2 cm long and 0.5 cm wide, glabrous, between Yellow Green 144A and Yellow Green 144B.

*Pedicel.*—Grows to 1.7 cm long and 1 mm wide, glabrous, between Yellow Green 144A and Yellow Green 144B.

*Bloom period.*—Mid June to November in Canby, Oreg.

Flower Bud:

*Size.*—4.3 cm long and 0.7 cm wide at the widest area.

*Description.*—Tubular, pendulous.

*Color.*—Between Yellow 5B and Yellow 5C.

Flower:

*Type.*—Zygomorphic, perfect.

*Shape.*—Tubular.

*Size.*—Grows to 6 cm long and 1.9 cm wide.

*Corolla description.*—Grows to 4.4 cm long and 1.8 cm wide; both sides glabrous; tube 4.3 cm long, swollen to 5 cm wide on bottom side for 0.4 cm under the calyx then narrows to 0.4 cm wide and expanding to 0.8 cm wide below the lobes; 5 lobes, reflexed, oblong, tips obtuse, margins entire, lobes 1 cm long and 0.6 cm wide; both sides Yellow 5B.

*Calyx description.*—0.8 cm deep and 0.8 cm wide, 5 spreading, slightly reflexed lobes cut almost to the base, glabrous inside and out, each lobe lanceolate in shape, 0.7 cm long and to 0.2 cm wide, margins entire, tip acute, closest to Yellow Green 144A.

*Pistil description.*—1, 6 cm long, ovary 0.5 cm long and 0.3 cm wide, Yellow Green 144B; style 5.5 cm long and less than 1 mm wide, Yellow Green 150C; stigma 1 mm Yellow Green 144B.

*Stamen description.*—4, filaments: two short 1.7 cm long and two long 1.8 cm and 1 mm wide, Green Yellow 1D, anthers 0.3 cm long and 0.2 cm wide, Greyed Orange 166A.

*Pollen.*—None seen.

*Fragrance.*—None.

*Lastingness.*—A flower lasts about a week on a plant.

Fruit:

*Type.*—Capsule, curved.

*Fertility.*—Moderate.

*Size.*—1 cm deep and 5 mm wide.

*Color.*—Brown 200D.

Seed: None seen.

Pests and Diseases: Plants of the new *Phygelius* have not been observed to be resistant to pathogens and pests common to *Phygelius*.

I claim:

1. A new and distinct cultivar of *Phygelius* plant substantially as shown and described.

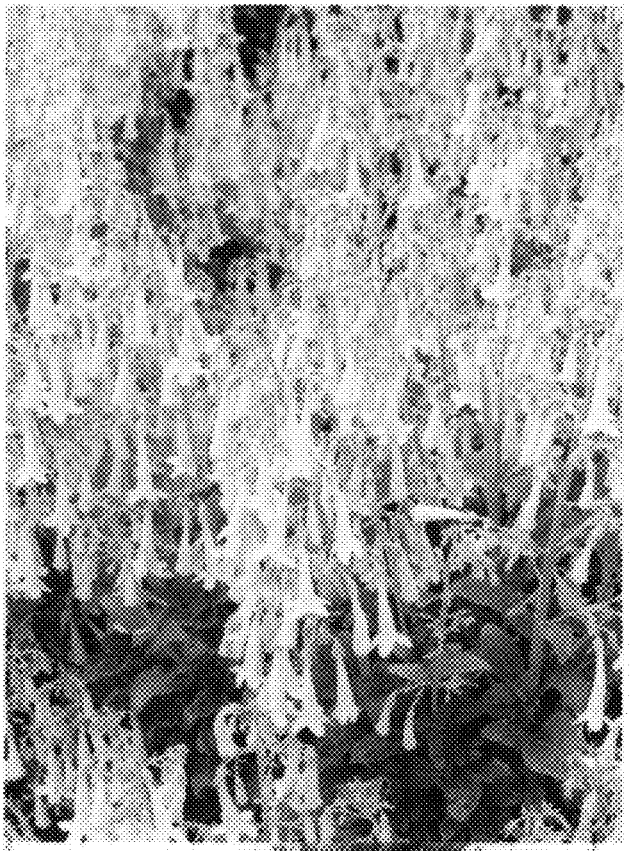
Fig. 1
Fig. 2
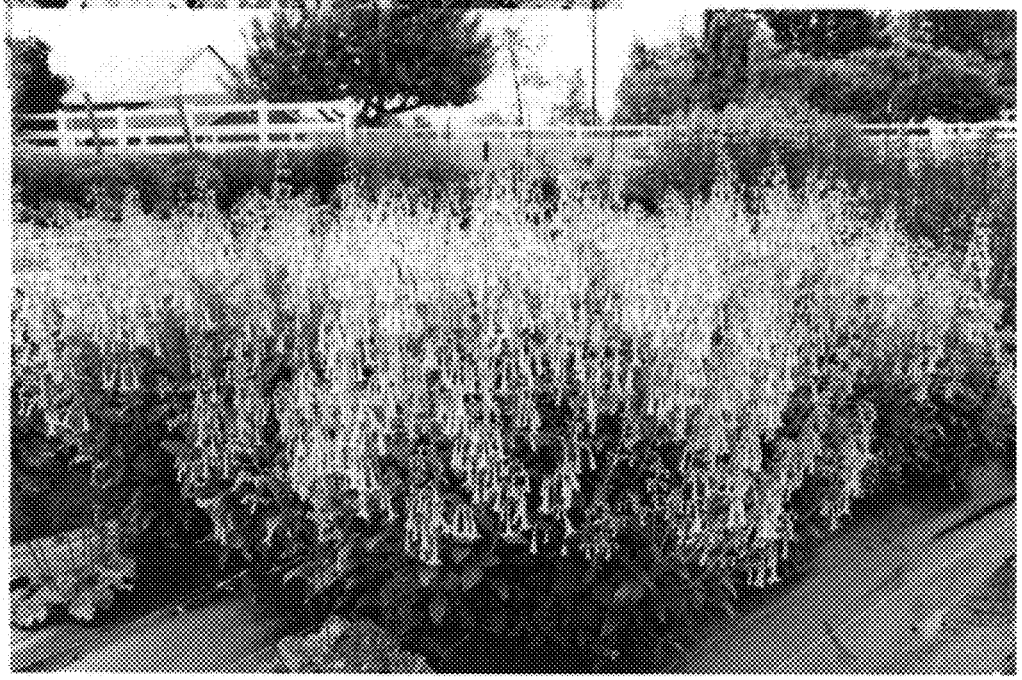

* * * * *